(12) United States Patent
Sinha (10) Patent No.: US 6,528,041 B2
(45) Date of Patent: Mar. 4, 2003

(54) PROCESS FOR THE PREPARATION OF 1-PROPYL-2, 4, 5-TRIMETHOXYBENZENE FROM TOXIC β-ASARONE OF ACORUS CALAMUS OR FROM CRUDE CALAMUS OIL CONTAINING β-ASARONE

(75) Inventor: Arun Kumar Sinha, Himachal Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/957,867

(22) Filed: Sep. 21, 2001

(65) Prior Publication Data

US 2002/0035299 A1 Mar. 21, 2002

Related U.S. Application Data

(62) Division of application No. 09/652,376, filed on Aug. 31, 2000.

(51) Int. Cl.$^7$ ............................. C11D 3/50; A61K 7/26; A61K 7/46; A61K 35/78; A24B 15/30
(52) U.S. Cl. ................. 424/58; 424/49; 424/195.1; 512/5; 131/275
(58) Field of Search ............................. 424/58, 191.1; 512/5

(56) References Cited

U.S. PATENT DOCUMENTS 5,186,722 A * 2/1993 Cantrell et al. ............... 44/605
5,700,449 A * 12/1997 Katayama et al. ............ 424/49

OTHER PUBLICATIONS

Arctander Perfume & Flavor Materials of Natural Origin "*Calamus Oil*" (col. 111–113), 1960.*
Steinmetz Codex Vegetabalis Entry 24 Acorus Calamus, 1953.*
Holking A Dictionary of Terms in Paarmacognosy Online Acoro, Acorus Calamus, Calamus Root, 1955.*

* cited by examiner

*Primary Examiner*—Shep K. Rose
(74) *Attorney, Agent, or Firm*—Ladas & Parry (57) ABSTRACT

The invention relates to a process for the preparation of 1-Propyl-2, 4, 5-trimethoxybenzene useful as a aroma molecule and as a starting material and intermediate for preparation of various drugs. The process comprises providing crude calamus oil or β-asarone in a solvent; hydrogenating the solution in the presence of a catalyst; filtering the catalyst and removing the solvent under reduced pressure; subjecting the reduced calamus oil to column of silica gel chromatography using an eluent to obtain the desired product in liquid form with 85–97% purity.

1 Claim, 6 Drawing Sheets

UV-vis spectra of ( i ) 1-Propyl-2,4,5-trimethoxybenzene and its comparison with ( ii ) β-asarone ( 2,4,5-trimethoxy-1-propenylbenzene ).

Gas Chromotogram of β-asarone with minor presence of α-asarone

Gas Chromotogram of1-Propyl-2,4,5-trimethoxybenzene

Electro spray (ES) mass spectrum of 1-Propyl-2,4,5-trimethoxybenzene (MW 210)

PROCESS FOR THE PREPARATION OF 1-PROPYL-2, 4, 5-TRIMETHOXYBENZENE FROM TOXIC β-ASARONE OF ACORUS CALAMUS OR FROM CRUDE CALAMUS OIL CONTAINING β-ASARONE

This application is a divisional of copending application Ser. No. 09/652,376 filed on Aug. 31, 2000.

FIELD OF THE INVENTION

The present invention relates to an improved process for the preparation of 1-Propyl-2,4,5-trimethoxybenzene of the formula I from the toxic compound β-asarone of *Acorus calamus* or from crude calamus oil containing β-asarone. The present invention also relates to a process for the preparation of 1-Propyl-2,4,5-trimethoxybenzene from toxic compound β-asarone of *Acorus calamus* or from crude calamus oil containing β-asarone and useful as a new kind of aroma molecule. The present invention also relates to a process for the preparation of salicylamide based antipsychotic drug from 1-Propyl-2, 4, 5-trimethoxybenzene, and other uses thereof.

BACKGROUND OF THE INVENTION

β-asarone (cis-2,4,5-trimethoxy-1-propenylbenzene) is found in a number of plants such as *Orthodon calveriei Level* and *Acorus gramineus* (Nguyen, X. D.; Ladinh, M, Vuviet, N.; Luudam, C. and Leclercq, P. A., J. of Essential Oil Research 7(1):111–112 (1995) and Perrett, S. and Whitfield, P. J., Phytotherapy Research 9(6):405–409 (1995)). Among all the plants, the highest percentage of β-asarone is present in tetraploid and hexaploid varieties of *Acorus calamus* (Rost, L. C. M., Planta Medica 36:350 (1979); Srivastava, M., Saxena, A. and Baby, P., Orient. J. Chem., 13(1): 97–98 (1997); Tang, W. and Eisenbrand, G., Chinese Drugs of Plant Origin, Springer-verlag, New York, 45–46 (1992) and Kaul, M. K., Medicinal Plants of Kashmir & Ladakh, Indus Publishing Company, 92–93 (1997)).

*Acorus calamus Linn*, a member of the family of Araceae, commonly known as "sweet flag", is a perennial plant (Grieve, M., A Modern Herbal, Tiger Books International, London, 726–729 (1998)) that grows in the wild along swamps, brooks, rivers and lakes worldwide. The plant is also cultivated widely in India, Pakistan, Bangladesh, China, Japan, Poland, Hungary, Yugoslavia, Bulgaria, USSR, Holland, USA and several other countries because of its varied medicinal activities and the great demand for its essential oil in the flavour and perfumery industries, in alcoholic beverages and for its antibacterial, antifungal and insecticidal properties (Treben, M. Health Through God's Pharmacy, Wilhelm Ennthaler, Steyer, Austria, 12–14 (1986); Akitar, H.; Virmani, O. P.; Popli, S. P., Misra, L. N., Gupta, M. M., Srivastava, G. N., Abraham, Z. and Singh, A. K., Dictionary of Indian Medicinal Plants, CIMAP, RSM Nagar, Lucknow, 10–11 (1992); Motley, T. J., Economic Botany, 48: 397–412 (1994) and Lawrence, B. M. and Reynolds, R. J., Perfumer & Flavorist 22(2):59–67 (1997)). However, photochemical reports on *Acorus calamus* reveals that the qualitative and quantitative composition of calamus oil and particularly the percentage of asarone is greatly affected by the location, growth stages and the species of *Acorus calamus*. A lot of discrepancy and variability has been noticed in asarone percentage of Asian and American calamus oil. It has been found that the oil of diploid plants (N. American) does not contain the carcinogenic compound β-asarone at all. The triploid race (E. European) contains limited amount of β-asarone varying from 3 to 8% and is therefore, usable in terms of both clinical effectiveness and safety (Stahl, E. and Keller, K., Planta Medica 43:128–140 (1981)). However, calamus oil originating from tetraploid or hexaploid varieties distributed extensively in Asian countries like India, Japan, Pakistan and China, contains a very high percentage of β-asarone varying from 70 to 90% (Waltraud, G. and Schimmer, O., Mutation Research 121:191–194 (1983); Mazza, G., J. of Chromatography 328:179–206 (1985); Nigani, M. C.; Ateeque, A.; Misra, L. N. and Ahmad, A., Indian Perfumer 34: 282–285 (1990) and Bonaccorsi, I.; Cortroneo, A.; Chowdhury, J. U. and Yusuf, M., Essenze Derv. Agrum, 67(4): 392–402 (1997)). The higher percentage of β-asarone is experimentally proved to be carcinogenic in animals and was found to induce tumours in the duodenal region after oral administration (Taylor, J. M.; Jones, W. I.; Hogan, E. C.; Gross, M. A.; David, D. A. and Cook, E. L., Toxicol. Appl. Pharmacol. 10:405 (1967); Keller, K.; Odenthal, K. P. and Leng, P. E., Planta Medica 1:6–9 (1985) and Riaz, M.; Shadab, Q.; Chaudhary, F. M., Hamdard Medicus 38(2); 50–62 (1995)). In addition, β-asarone has also shown chromosome damaging effect on human lymphocytes in-vitro after metabolic activation (Abel, G., Planta Medica 53(3): 251–253 (1987)). As a result, the use of this well known medicinal plant which had been in use for many years, is now prohibited in flavour, perfumery and human food (Harborne, J. B. and Baxter, H., Phytochemical Dictionary: A Handbook of Bioactive Compounds from Plants, Taylor & Francis Ltd., Washington D.C., 474 (1993) and McGuffin, M., American Herbal Products Association's Botanical Safety Handbook, CRC Press, Inc., Boca Raton Fla., USA, 231 (1997)).

The oil and extracts of *Acorus calamus* have been reported to have numerous pharmacological activities. Some of the active ingredients found therein are glucosides, sitosterol (Patra, A. and Mitra, A. K., Indian J. Chem., Sec B, 17B:412 (1979), amino acids, acoramone (Patra, A. and Mitra, A. K., J. of Natural Products 44(6):668–669 (1981), flavones, fatty acid, sesquiterpene named calamnonone (Wu, Li.; Xiang, T.; Liu, T., Li, M.; Gao, Z. and Meng, X., Bopuxue Zazhi 15 (3):249–251 (1998) and triterpenoid saponins (Rai, R., Siddiqui, I. R. and Singh, J., Indian J. Chem., Sec B, 37 B(5), 473–476 (1998)) Modern applications of the *Acorus calamus* plant include its use in cleansing of facial skin (Horste, B.; Sarma, I.; Gercikovs, I. and Gordejeva, V., L. V. Patent No. 92-920022, issued May 28, (1992); germination inhibitors (Nawamaki, K. and Kuroyanagi, M., Phytochenistry 43 (6):1175–1182, (1996); in formulation for alcoholic bitters (Sargunas, G.; Daniuniene, G.; Talacka, C.; and Aleksiunas S., L. T. Patent No. 36793, issued Jan. 25, (1996) and for the prevention and improvement of vision disorders (Mihara, T., JP Patent No. 10324636 A2, issued Dec. 8, (1998)).

*Acorus calamus*, known as "vaich" in Hindi, has also been credited with many medicinal properties from ancient ties in Ayurvedic system of India (Vohora, S. B.; Shah, S. A. and Dandiya, P. C., J. of Ethnopharmacology 28(1): 53–62 (1990); Rastogi, R. P. and Mehrotra, B. N., Compendium of Indian Medicinal Plants, 1:1, (1990), C. S. I. R., New Delhi and Asolkar, L. V., Kakkar, K. K. and Chakre, O. J., Glossary of Indian Medicinal Plants with Active Principles, Publications & Information Directorate (C. S. I. R), New Delhi, Part-I, 18–20 (1992)). It is known for more than 2000 years in China for treating a number of disorders (Albert, Y. L., Encyclopaedia of Common Natural Ingredient Used in Food, Drugs and Cosmetics, ed, John Wiley & Sons Inc. New York, 111–112 (1996)). However, all the above uses and medicinal potential of Acorus calamus have been hampered because of carcinogenic effect of β-asarone (Opdyke, D. L. J., Food Cosmet. Toxicol., 15: 623, (1997)). α-Asarone is also reported to be fatal in rats (Lopez, M. L.; Hernandez, A.; Chamorro, G. and Mendoza, F. T., Planta Medica 59(20) :115–120 (1993) and Chamorro, G., Salazar, M., Salazar, S. and Mendoza, T., Revista-de-Investigation-Clinica 45(6) :597–604 (1993)). As a result, countries such as India, Pakistan, Bangladesh, Japan and China where plants of tetraploid and hexaploid origin contain 70 to 90% β-asarone are most affected by the prohibition on the use of calamus oil.

The levels of β-asarone can be easily detected by IR-spectroscopy (Stahl, E. and Keller, K, Pharmazie 36(1) :53–57 (1981); HPTLC (Narayana, D. B. A.; Raghuvanshi, P; Agarwal, S. and Srinivas, K. S., Indian Drugs 32(6) :254–257 (1995); densitometry (Tamas, M.; Oprean, R. and Roman, L., Farmacia (Bucharest) 44 (5–6): 13–21 (1996)); gas chromatography (Baxter, R. M.; Dandiya, P. C.; Kandel, S. I.; Okanya, A. and Walker, G. C., Nature 185:466–467 (1960) and Spilkova, J. T.; Tomasch, J.; Vavra R. and Dusek, J, Ceska Slov. Farm., 45 (3): 146–148 (1996)) and GC-MS (Oprean, R.; Tamas, M. and Roman, L., J Pharm. Biomed. Anal., 18 (1,2): 227–234 (1998)).

Separation of β-asarone from calamus rhizomes (americanus var.) by supercritical extraction (Stahl, E. and Keller, K., Planta Medica 47 (2): 75–78 (1983)) or by raising plants on alkaline soil (Chowdhary, A. R.; Gupta, R. C. and Sharma, M. C., Indian Perfumer 41 (4): 154–156 (1997)) have been developed. However, these methods do not effectively lower the high percentage (70 to 90%) of asarone content of tetraploid or hexaploid varieties. It is therefore imperative to provide a simple chemical process by which β-asarone or crude calamus oil can be easily modified to reduce its carcinogenic effect rather than by reduction in the percentage of asarones by any other means. While supercritical gas extraction of calamus oil (americanus variety) with fractionated separation has been reported (Keller, K. and Stahl, E., Planta Medica 47(2): 71–74 (1983)) to make β-asarone free calamus oil, fractionation will not be cost effective with tetraploid or hexaploid varieties having very high percentage of β-asarone (70 to 90%).

Interest in development of a simple and economical chemical process to reduce the toxicity of carcinogenic compound β-asarone by elimination of side double bond continues to be strong as evidenced by numerous literature reports that show that the double bond of asarone is responsible for bioactivity and photooxidation. A detailed literature survey reveals that calamus oil has been found active as antigonadal, antifeedant and growth inhibitory in insects. The activities of calamus oil are found due to the presence of double bond in the alkyl side chain and cis configuration of β-asarone (Saxena, B. P.; Koul, O.; Tikku, K.; Atal, C. K. and Opender, K., Nature, London, 270(5637): 512–513 (1977); Koul, O., Sci. Acad. Medal Lectures, Ed. INSA, New Delhi, India, 62 (1979) and Koul, O.; Smirle, M. J. and Isman, M. B., J. Chem. Ecol. 16:1911–1920 (1990)). The side double bond forms asarone epoxide and asarone diol which is identified in the insect excreta of Peridroma saucia larvae (Noctuidae: Lepidoptera) (Koul, O.; Smirle, M. J.; Isman, M. B. and Szeto, Y. S., Experientia 46:1082–1084 (1990)). The double bond of β-asarone is also found to be photosensitive and while standing the calamus oil on long storage without exclusion of air and light, the oil got contaminated with photo-oxidised products such as asaraldehyde and dimer (Saxena, D. B. and Mukerjee, S. K., Indian J. Chemistry, Sec B, 24 B: 683–684 (1985)), Recently, a number of photoxidised product formations were also studied by light induced transformation of β-asarone in ethanolic solutions (Lander, V. and Schreier, P., Flavour Fragrance J. 6(1) 21–28 (1991)). Based on the above survey, it appears logical to develop a convenient chemical process for utilising the side double bond of β-asarone to reduce its toxicity.

It is reported that the side double bond of isolated β-asarone of Acorus calamus or crude calamus oil is reduced either over Pd, Pt, Pd(OH)$_2$, PtO$_2$, BaSO$_4$/Pd, Raney nickel and ammonium formate to obtain 1-Propyl-2,4,5-trimethoxybenzene with improved properties such as an aroma that is better than the pungent smell of β-asarone (Joseph G. C.; Clare, D T.; John, P. L., Ranbir, K. B.; Paul, L. and Jan, R. F., J. Med. Chem. 32:2210:2214 (1989); Christopher, I., Fincham, M. H.; David, R. H.; David, C. H., John, C. O.; Giles, S. R.; David, C. R. and Edward, R., J. Med. Chem. 35:1472–1484 (1992) and Tomoyuki, Y.; Ryo, N., Toru, K.; Shinichi, T.; Tamako, N.; Tokio, Y. and Toshiyasu, M., J. Med. Chem. 40:1252–1257 (1997)).

The reaction schemes of the processes are given below:

SCHEME I

SCHEME II

The olfactory assessment of 1-Propyl-2,4,5-trimethoxybenzene is performed as per Indian standard of 2284, 1997 (Bureau of Indian Standard, Manaki Bhavan, 9 Bahadur Shah Zafar Marg, New Delhi). The odour effect perceived by the olfactory nerves on smelling a strip impregnated with an oil is revealed as sweet, ylang, slightly spicy and fruity thereby enabling use as multipurpose additives in the areas of mouthwash, tooth paste, antiseptic soap products, chewing gum flavour and little in spicy products. In addition, it was observed that the product 1-Propyl-2,4,5-trimethoxybenzene is a simple and an economical starting material for synthesis of salicylamide based antipsychotic drugs (5,6-dimethoxy-N[(1-ethyl-2-pyrrolidinyl)methyl]-3-propylsalicylamide).

The salicylamide derivative displays high and stereoselective affinity for the [3H] spiperone and [3H] raclopride binding sites in vitro (dePaulis, T.; Kumar, Y., Johansson, L; Ramsby, S.; Florvall, L; Hall, H.; Angeby, M. K. and Ogren, S O., J. Med. Chem 28, 1263–1269(1985) and dePaulis, T.; Kumar, Y.; Johansson, L., Ramsby, S.; Hall, H.; Sallemark, M; Angeby, M. K. and Ogren, S. O., J. Med. Chem. 29:61–69 (1986)). Recently, Hogberg T., Stefan, B.; Tomas, D. P.; Lars, J.; Peter, S; Hakan, H. and Ogren, S. O., J. Med. Chem. 33 1155–1163 (1990) have synthesized a series of 3-substituted salicylamide derivatives in which the presence of 3-propyl group and 5,6-dimethoxy group at salicylamide ring shows a very high and stereoselective affinity for the dopamine-$D_2$ receptor. However, the reported synthesis for salicylamide derivative involved several steps in which intermediate 1-Propyl-2,4,5-trimethoxybenzene is itself synthesized in two steps by Friedel-Craft acylation of an expensive material 1,2,4-trimethoxybenzene with propyl-chloride followed by catalytic hydrogenation with an overall in lower yield (reaction scheme given below as Scheme III).

SCHEME III

OBJECTS OF THE INVENTION

The main object of the present invention is to develop a process for the preparation of 1-propyl-2,4,5-trimethoxybenzene from high toxic compound β-asarone present in the asarone bearing varieties of *Acorus calamus* or from crude calamus oil containing β-asarone obtained therein.

It is another object of the invention to develop a process for the preparation of 1-propyl-2,4,5-trimethoxybenzene which is useful as a new kind of aroma molecule with multifarious applications.

It is another object of the invention to develop a process for the preparation of 1-propyl-2,4,5-trimethoxybenzene which is useful as a starting material for salicylamide based antipsychotic drugs.

Another object of the present invention is to provide a simple process for isolation of β-asarone in high purity from *Acorus calamus* oil.

Still another object of the present invention is to provide a simple process for the preparation of 1-Propyl-2,4,5-trimethoxybenzene by catalytic reduction of above isolated β-asarone.

Yet another object of the present invention is to provide a simple and an inexpensive process for the preparation of 1-Propyl-2,4,5-trimethoxybenzene by direct reduction of calamus oil in which the percentage of asarones (including α, β and γ-asarone) go upto 90% in tetraploid or hexaploid varieties of *Acorus calamus* oil.

Yet another object of the present invention is to provide 1-Propyl-2,4,5-trimethoxybenzene as an inexpensive and simple starting material for synthesis of several drugs, for example salicylamide based antipsychotic drugs.

Yet another object of the present invention is to eliminate or minimize the toxicity of calamus oil of tetraploid or hexaploid varieties of Asian countries, thereby enhancing the profitable use thereof.

Yet another object of the present invention is to provide a simple reduction process in converting essential oils of other asarones rich plants such as *Asarium europaeum, Crowea angustifolia* and *Heterotropa yakusimensis* into useful products such as 1-Propyl-2,4,5-trimethoxybenzene for use in the flavour, perfumery and pharmaceutical industries.

SUMMARY OF THE INVENTION

Accordingly, the present invention relates to a process for the preparation of 1-Propyl-2,4,5-trimethoxybenzene of the formula I useful as a aroma molecule and as a starting material and intermediate for preparation of various drugs.

I the said process comprising the steps of
(a) providing crude calamus oil or β-asarone in a solvent selected from the group consisting of ethanol, methanol, THF, DCM, Toluene and chloroform
(b) hydrogenation of the solution in the presence of a catalyst selected from the group comprising of Pd/C, Pt, Pd(OH)$_2$, Raney nickel and ammonium formate at a pressure in the range of 10–40 psi hydrogen gas and at a temperature in the range of 15–40° C.;
(c) filtering the catalyst and removing the solvent under reduced pressure in the range of 10–100 mm Hg;
(d) subjecting the reduced calamus oil to column or silica gel chromatography using an eluent to obtain the desired product in liquid form with 85–97% purity.

In one embodiment of the invention the catalyst comprises 5–10% Pd/C.

In another embodiment of the invention, the calamus oil used is of tetraploid or hexaploid origin.

In yet another embodiment of the invention, a new kind of honey and rose aroma is detected in the case of reduced calamus oil.

In yet another embodiment of the invention, a new kind of sweet, ylang, slightly spicy and fruity aroma is detected in case of 1-Propyl-2,4,5-trimethoxybenzene.

In another embodiment of the invention, the reduced calamus oil is useful in the toiletry soap, shaving cream and tobacco products.

In another embodiment, the invention relates to the use of 1-Propyl-2,4,5-trimethoxybenzene as a multipurpose additive in mouthwash, tooth paste, antiseptic soap products, chewing gum flavour and in spicy products.

In a further embodiment, the invention relates to the use of 1-Propyl-2,4,5-trimethoxybenzene as an inexpensive and simple starting material for the preparation of the 3-propyl-5,6-dimethoxysalicylamide based antipsychotic drug 5,6-dimethoxy-N[(1-ethyl-2-pyrrolidinyl)methyl]-3-propylsalicylamide.

In another embodiment, the invention relates to the conversion of 1-Propyl-2,4,5-trimethoxybenzene to products which can be used for flavour, perfumery industries and as starting material for various important drugs and for new organic compounds by bromination, oxidation, reduction, coupling reaction, allylic hydroxylation, dimerisation, formylation, Grignard reaction, oxymercuration-demercuration, demethylation, alkylation and epoxidation.

In a further embodiment of the invention, the crude calamus oil is extracted front asarone rich plants such as *Asarum europaeum, Crowea angustifolia* and *Heterotropa yakusimensis.*

In another embodiment of the invention, the toxicity of the reduced calamus oil is two times less than that of the starting crude calamus oil.

In another embodiment of the present invention a simple catalytic hydrogenation of either β-asarone of *Acorus calamus* or calamus oil is described to obtain 1-Propyl-2,4,5-trimethoxybenzene or reduced calamus oil with a new kind of sweet, fruity, spicy and honey and rosy aroma for use flavour, perfumery and pharmaceutical industries.

In yet another embodiment of the present invention a simple catalytic process is described to convert other asarones rich plants such as *Asarum europaeum, Crowea angustifolia* and *Heterotropa yakusimensis* into useful products such as 1-Propyl-2,4,5-trimethoxybenzene for various applications.

DETAILED DESCRIPTION OF THE INVENTION

Figure 1:
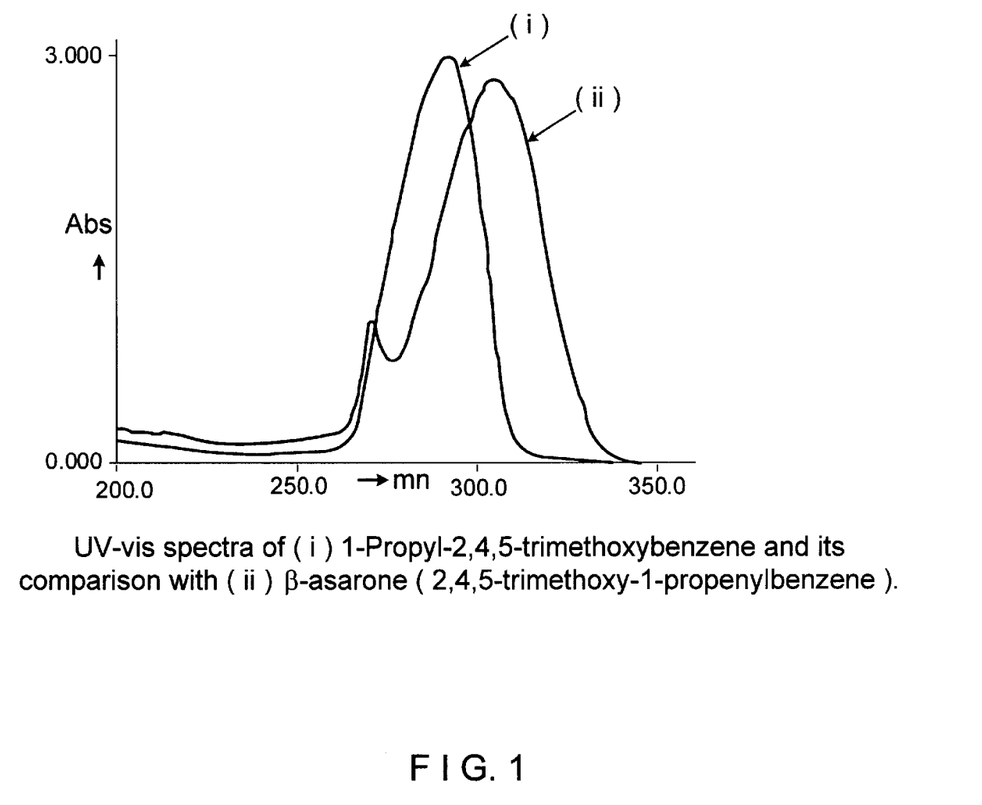
FIG. 1 is the UV spectra of 1-Propyl-2,4,5-trimethoxybenzene and its comparison with β-asarone (2,4,5-trimethoxy-1-propenylbenzene).

The present invention affords a single step synthesis of 1-Propyl-2,4,5-trimethoxybenzene by catalytic hydrogenation of calamus oil or β-asarone (cis-2,4,5-trimethoxy-1-propenylbenzene). The UV-vis spectra of 1-Propyl-2,4,5-trimethoxybenzene clearly show the loss of side double bond, as there was shift in absorbance by 13 nm (FIG. 1). In the first approach, β-asarone is isolated by column chromatography of calamus oil which gave a single spot of β-asarone with $R_f$ 0.63 (hexane:benzene/toluene:ethylacetate: 1:1:0.1) on silica gel TLC plate but its gas chromatography (tr=20.16 min) (performed on a Shimadzu-GC-14B gas chromatograph with the following conditions: SE-30 column; 30 m×0.25 mm; injector 250°/C.; FID detector 230°/C.; temp. programme 40 (hold for 2 min.) to 220° C. (hold for 10 min.), 10° C. min$^{-1}$; vol. 1 μl; $N_2$ flow 30 ml/min; $H_2$ flow 40 ml/min., air flow 300 ml/min; split injection ratio 1:30) has shown the purity in 94% (FIG. 2) with minor presence of other isomers α-asarone (tr=20.87 min) and/or γ-asarone. Since it was not very easy to separate β-asarone completely from α and γ-asarone on column chromatography due to the close resemblance in their structure, no efforts were made for further purification. β-asarone of 94% was used as such for catalytic reduction which gave a single spot of 1-Propyl-2,4,5-trimethoxybenzene with Rf 0.69 (hexane:benzene/toluene:ethylacetate: 1:1:0.1) on silica gel TLC plate and its purity was found 99% (FIG. 3) on gas chromatography (tr=19.78 min) indicating the reduction of β-asarone along with γ and α-asarone.

Figure 2:
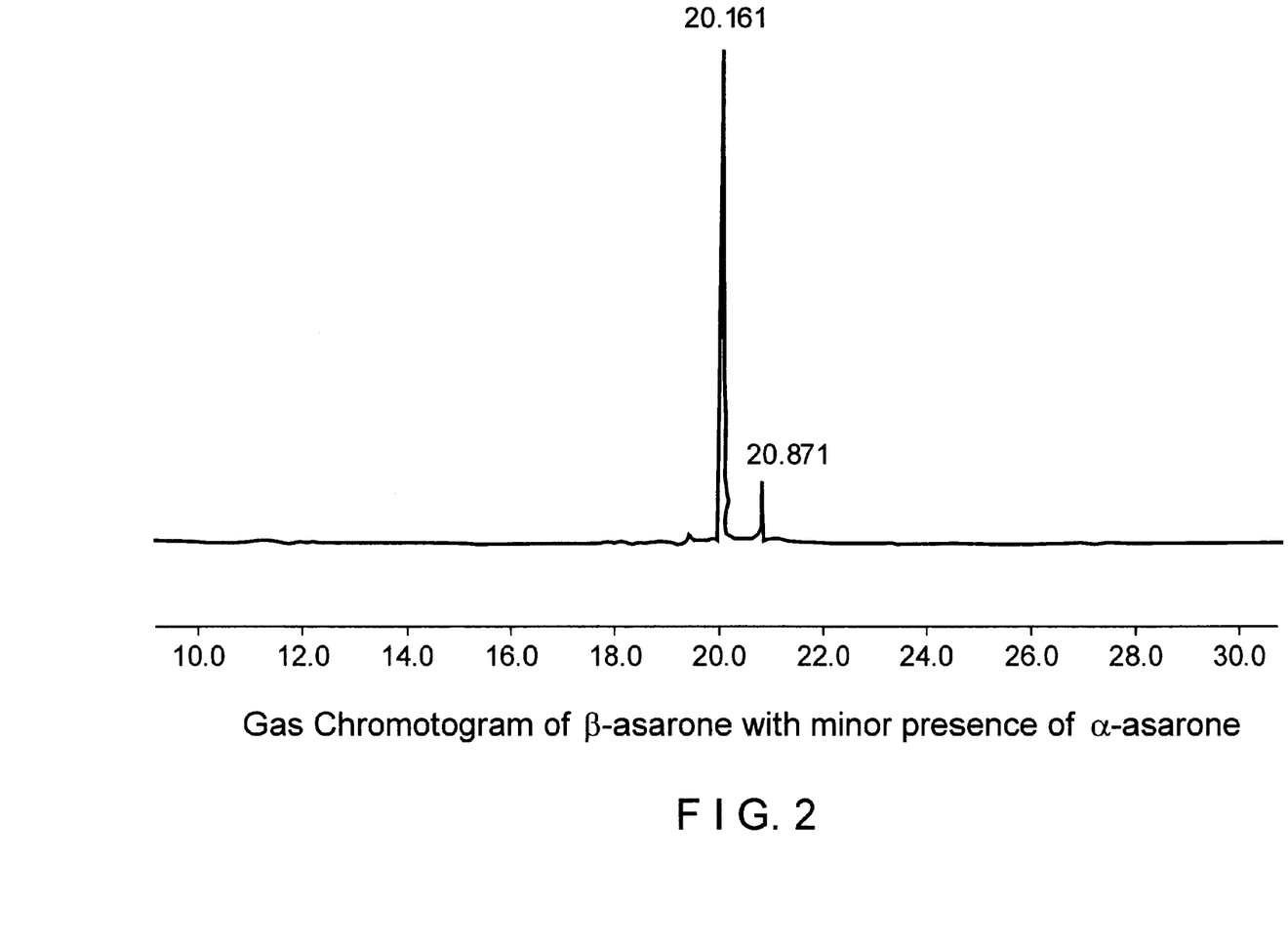
FIG. 2 is a gas chromatogram of β-asarone with minor presence of α-ASARONE.

Isolation of β-asarone from *Acorus calamus*: The pale yellow calamus oil (17.00 g) was chromatographed over silica gel using hexane as eluent to remove unwanted non-polar compounds. Subsequent elution with hexane-benzene mixture with increasing proportion of benzene gave 13.94 g of a pure liquid with 82% yield (w/w) with $R_f$ 0.63 on silica gel TLC plate (hexane:benzene/toluene:ethylacetate=1:1:0.1) whose electrospray (ES)-mass spectrum gave a molecular ion at m/e 208 (M+, 100), 193 (M$^+$-Me, 46), 165 (M$^+$-C3H$_7$, 24), suggesting the molecular formula $C_{12}H_{16}O_3$ in good agreement with the observation of 12 signals with peak at δ 125.5 (C-1'), 124.7 (C-2') and 14.5 (C-3') for side propenyl group and rest carbons at 151.4 (C-2), 148.5 (C-4), 142.3 (C-5), 118.0 (C-1), 114.1 (C-6), 97.6 (C-3) and 56.5, 56.2 & 55.9 (3-OCH$_3$) on the $^{13}$C NMR (CDCl$_3$, 75.4 MHz). The IR spectrum showed strong absorption at 1608 cm$^{-1}$, indicating the presence of an olefinic group and rest are at 2937, 2835, 1583, 1512, 1465, 1321, 1213, 1119, 1037, 965 and 859 cm$^{-1}$. The $^1$H NMR (CDCl$_3$, 300 MHz) signals showed a dd at δ 6.50 (1H, J=15.8 Hz and 1.5 Hz, H-1'), dq at 5.78 (1H, J=6.5 Hz and 15.8 Hz, H-2'), and 1.85 (3H, dd, J=6.5 Hz and 1.5 Hz, H-3') due to proton of propenyl side chain and rest protons at 6.84 (1H, s, H-6), 6.53 (1H, s, H-3), and 3.88, 3.83 and 3.79 (s, 3H, each, 3-OCH$_3$). UV λmax MeOH nm (log ε): 269 (2.36), 301 (4.01). On the basis of above spectral data and comparing with reported literature (Gonzalez, M. C.; Sentandrew, M. A.; Rao, K. S.; Zafra, M. C. and Cortes, D., Phytochemistry 43:1361–1364 (1996)), the liquid was identified as β-asarone in 94% purity (by GC) (FIG. 2)

Figure 3:
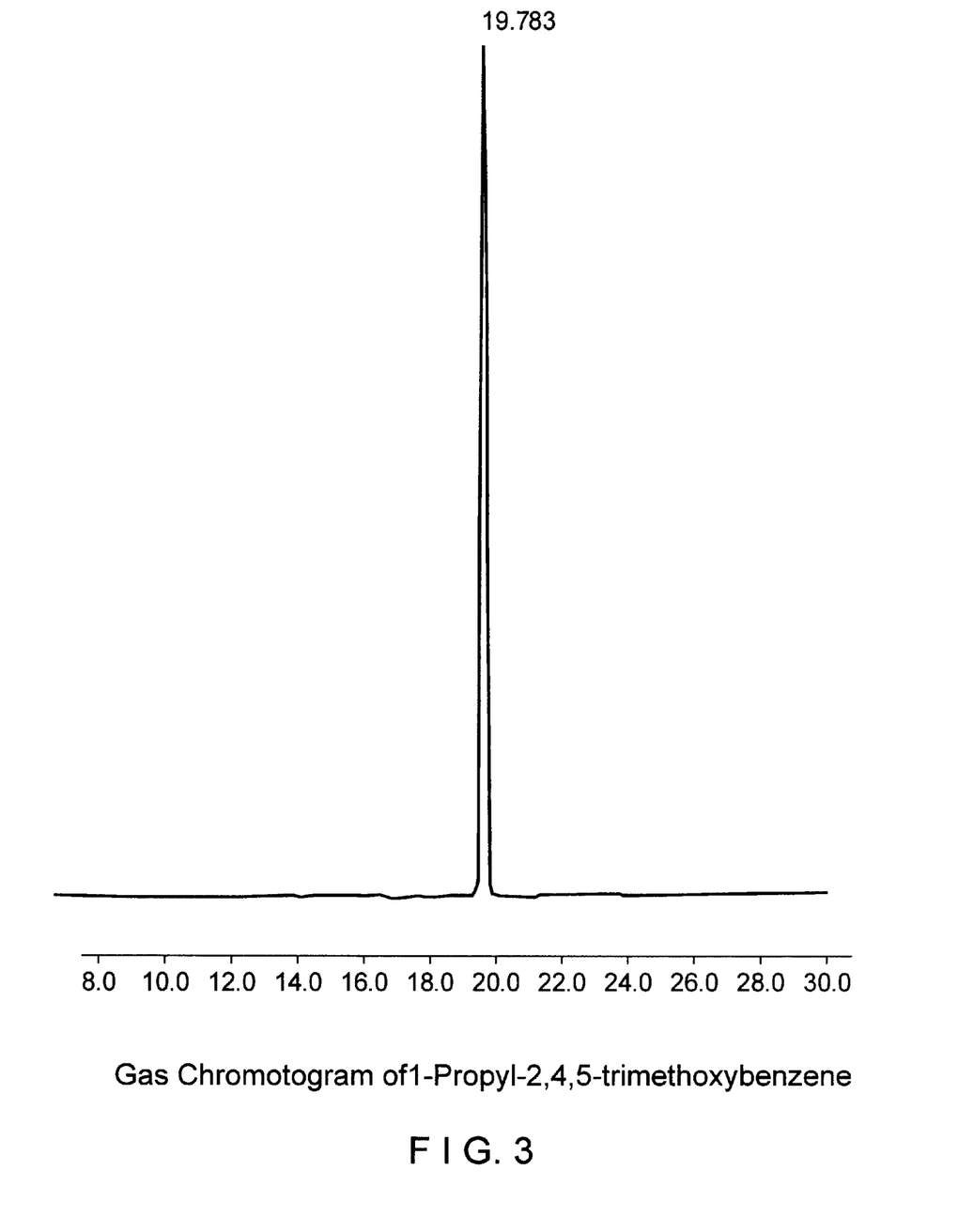
FIG. 3 is a gas chromatogram of 1-Propyl-2,4,5-trimethoxybenzene.
Figure 4:
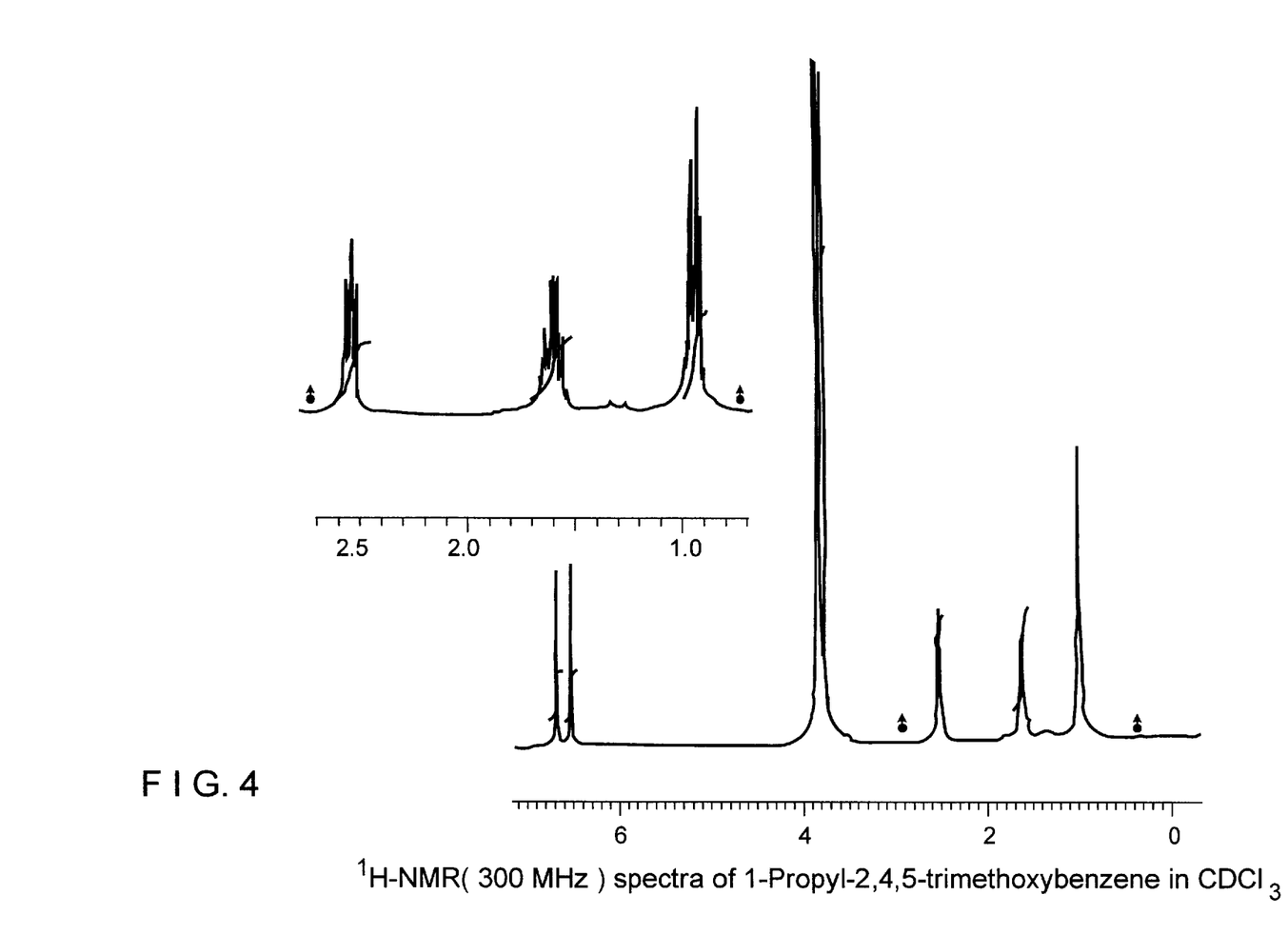
FIG. 4 is $^1$H NMR (300 MHz) of 1-Propyl-2,4,5-trimethoxybenzene in CdCl$_3$.
Figure 5:
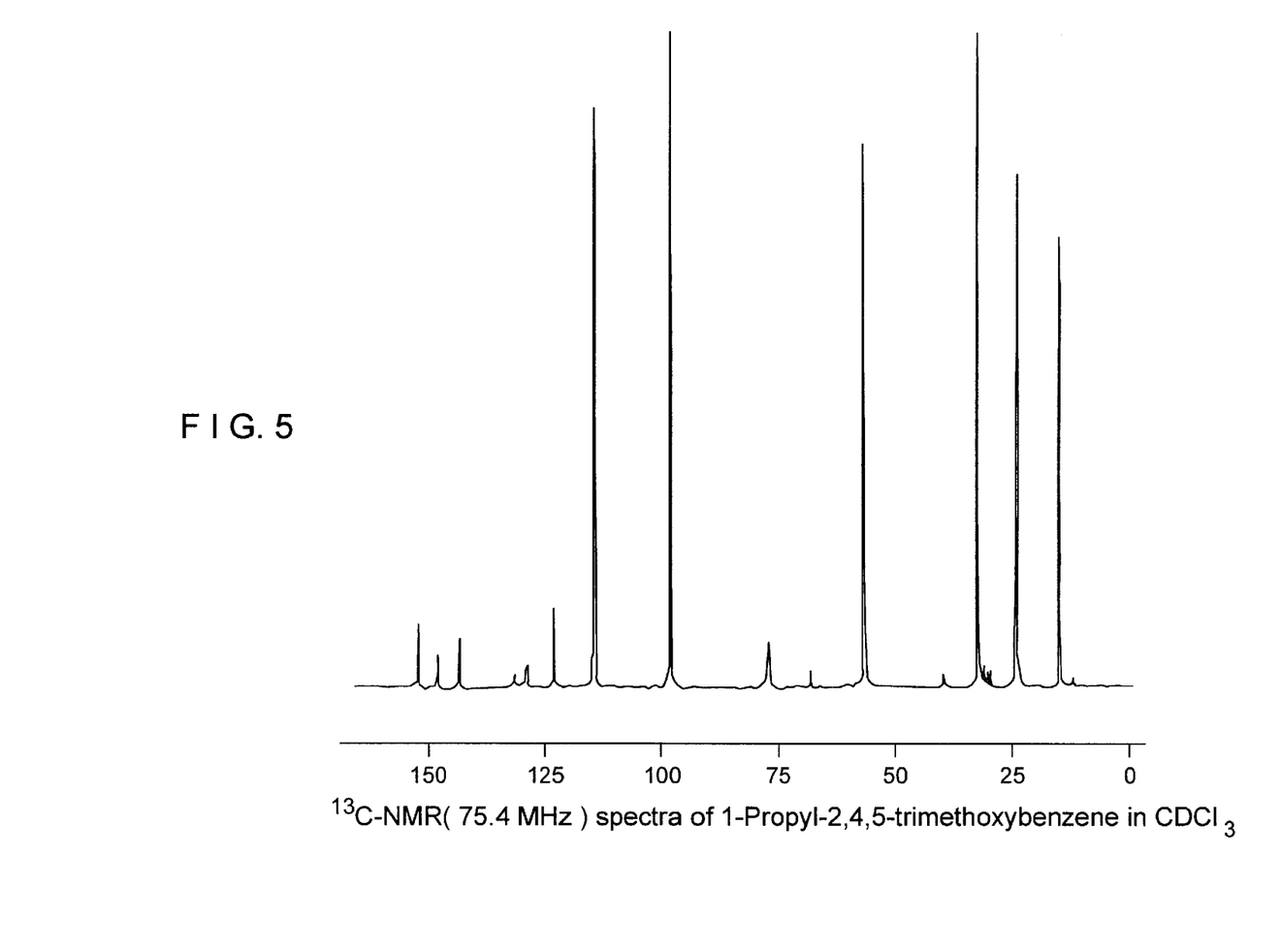
FIG. 5 is $^{13}$C-NMR (75.4 MHz) of 1-Propyl-2,4,5-trimethoxybenzene in CdCl$_3$.
Figure 6:
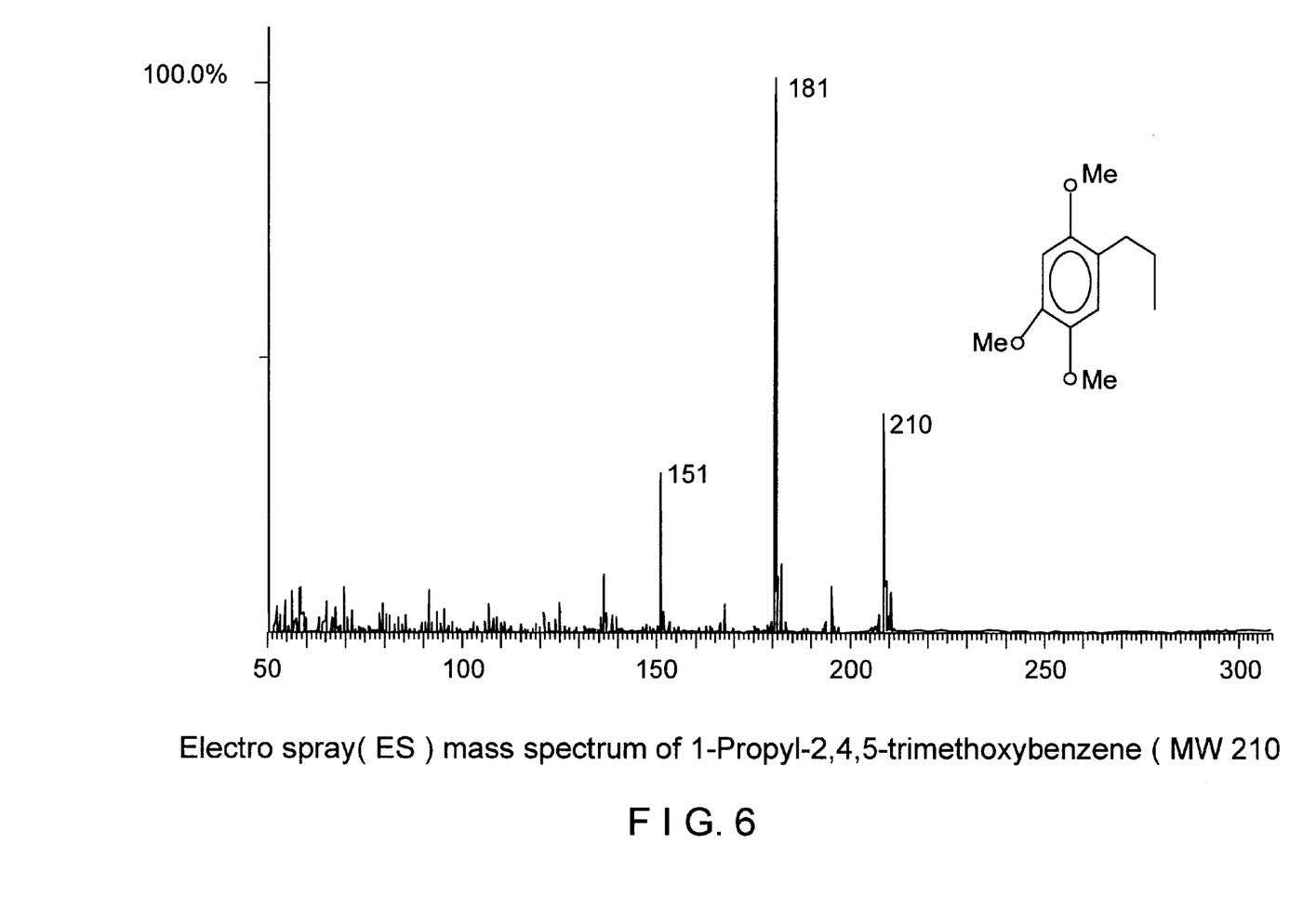
FIG. 6 is the electro spray (ES) mass spectrum of 1-Propyl-2,4,5-trimethoxybenzene (MW 210).

Synthesis of 1-Propyl-2,4,5-trimethoxybenzene from β-asarone: The β-asarone (6.00 g, 0.029 mol) in 160 ml of ethanol is stirred with 10% palladium on activated charcoal (0.80 g) and ammonium formate (17.00 g, 0.27 mmol) at room temperature under nitrogen atmosphere till the disappearance of starting material. The catalyst was removed by filtration and the solvent was evaporated under reduced pressure. The residue was partitioned between ethyl acetate and water and the ethyl acetate layer washed with water, dried (Na$_2$SO$_4$) and filtered. Evaporation of filtrate left a liquid, which was chromatographed, on silica gel using hexane-benzene mixture with increasing proportion of benzene as the eluent. The eluate was evaporated to give 5.87 g (97%) of a clear sweet and pleasant liquid with $R_f$ 0.69 (hexane:benzene/toluene:ethylacetate=1:1:0.1) which solidified below 0° C. The $^1$H NMR (DMSO-d6) of liquid showed an expected shift of proton of propyl side chain which appeared at δ d 2.5 (2H, t, C-1'), 1.6 (2H, m, C-2') and 0.9 (3H, t, C-3') and rest protons at 6.72 (1H, s, H-6), 6.62 (1H, s, H-3) and 3.76 to 3.68 (9H, s, 3-OCH$_3$). The mass spectrum of liquid showed a molecular ion at m/e 210 (M$^+$, 39), 181(M$^+$-C$_2$H$_5$, 100), 167 (M$^+$-C$_3$H$_7$, 5), 151 (M$^+$-OCH$_3$+CO, 29), 136 (M$^+$-C$_3$H$_7$+OCH$_3$, 10) which IR spectrum showing strong absorption at 2958, 2870, 1512, 1464, 1398, 1205, 1124, 1040, 978 and 843 cm$^{-1}$ with disappearance of olefinic absorption (1608 cm$^{-1}$). $^{13}$C NMR (CDCl$_3$) of liquid also showed expected shift of propyl side signals of C-1', C-2' and C-3' which appeared at δ 31.6 (C-1'), 23.3 (C-2') and 13.79 (C-3') and rest at δ 151.4 (C-2), 147.4 (C-4), 142.7 (C-5), 122.7 (C-1), 114.3 (C-6), 98.0 (C-3) and 56.5, 56.2 & 56.0 (3-OCH$_3$). UV λmax MeOH nm (log ε) 288 (4.28). A shift by 13 nm in UV-vis spectra of product was observed from 301 nm to 288 nm (as conjugation of double bond of starting material asarone was reduced to single bond) with complete disappearance of peak 269 nm (FIG. 1). On the basis of 1H NMR (FIG. 4), $^{13}$C NMR (FIG. 5) and Mass (FIG. 6) spectral data, the above liquid was identified as 1-Propyl-2,4,5-trimethoxybenzene of Formula I in 99% purity (by GC) (FIG. 3).

Synthesis of 1-Propyl-2,4,5-trimethoxybenzene from crude oil of *Acorus calamus*:

In this method 42.00 g of crude calamus oil in 300 ml methanol was hydrogenated with 10% Pd/C (4.80 g) at 10–40 psi at room temperature till the disappearance of starting material. The catalyst was filtered and the solvent was removed under reduced pressure, which afforded 39.9 g (95 w/v) of reduced oil. Column purification of reduced oil on silica gel column using above eluent system (hexane-benzene mixture) gave a liquid 35.76 g in 85% yield (w/w). The 1H NMR (CDCl$_3$) of liquid appeared at δ d 2.4 (2H, t, C-1'), 1.6 (2H, m, C-2'), 0.9 (3H, t, C-3'), 6.81 (1H, s, H-6), 6.32 (1H, s, H-3) and 3.84 to 3.78 (9H, s, 3-OCH$_3$). The GC, Mass spectra and UV-vis spectra of liquid confirmed the formation of 1-Propyl-2,4,5-trimethoxybenzene.

Synthesis of salicylamide based antipsychotic drug (5,6-dimethoxy-N[1-ethyl-2-pyrrolidinyl]methyl)-3-propylsalicylamide:

Synthesis of this drug is reported by Thomas, H.; Stefan, B., Tomas, D. P; Lars, J.; Peter, S.; Hakan, H.; and Ogren S. O., J. Med. Chem. 33: 1155–1163 (1990) and involved several steps, the details of which are given below:

i. 2,4,5-trimethoxypropiophenone: Aluminum chloride (18.6 g, 0.14 mol) was added to a solution of 1,2,4-trimethoxybenzene (23.4 g, 0.14 mol) and propionyl chloride (11.4 g, 0.14 mol) in 250 ml of CH$_2$Cl at 10° C. After stirring for 1 hour, standard work up and recrystallisation from MeOH gave 25.0 g (80%) of pure product (i), mp 108–110° C. Anal (C$_{12}$H$_{16}$O$_4$) C,H,O. (Other spectral data such as NMR, Mass is not mentioned).

ii. 1-propyl-2,4,5-trimethoxybenzene: It was prepared by hydrogenation (4.5 1 H$_2$, 0.2 mol) of the corresponding propiophenone (i) (22.4 g, 0.1 mol) in 350 ml of MeOH at normal pressure with palladium on charcoal (5%, 2.3 g) as catalyst. Filtration and evaporation gave 20 g (0.1 mol) of an oil (ii) which lithiated directly. (Spectral data such as NMR, Mass is not given).

iii. 3-propyl-2,5,6-trimethoxybenzoic acid: It was prepared by addition of butylliium to a solution of 1-propyl-2,4,5-trimethoxybenzene (ii) in anhydrous THF under $N_2$ at 20–30° C. After stirring for 1.5 hours the reaction mixture was poured into solid carbon dioxide in $Et_2O$. Water was added and the phases were acidified with concentrated HCl and extracted with $CH_2Cl_2$. Evaporation of the solvent provided a crude acid (iii) contaminated with some pentanoic acid: $^1H$ NMR ($CDCl_3$) δ 6.8 (s, 1), 3.8–3.9 (3s, 9), 2.4 (t, 2), 1.6 (m, 2), 0.9 (t, 3). Characterised as primary amide (iii), mp 130–131° C. (i-$Pr_2O$).

iv. (S)-3-propyl-N-[(1-ethyl-2-pyrrolidinylmethyl)-2,5,6-trimethoxybenzamide]: A solution of 3-propyl-2,5,6-trimethoxybenzoic (iii), thionyl chloride and a few drops of dimethylformamide in toluene was stirred at 60° C. for 1 hour. The solvent was evaporated and the residue was dissolved in $CHCl_3$ and evaporated again. The residual acid chloride was dissolved in $CHCl_3$ and a solution of (S)-2-(aminomethyl)-1-ethylpyrrolidone in 40 ml of $CHCl_3$ was added. The temperature rose to 50° C. during addition. After stirring for 30 minutes, the solvent was evaporated and the residue was partitioned between 1M NaOH and $Et_2O$. After additional extraction of the aqueous phase with $Et_2O$, the combined ethereal extract were dried and evaporated to give (S)-3-propyl-N-[(1-ethyl-2-pyrrolidinylmethyl]-2,5,6-trimethoxybenzamide (iv) in 32% yield, mp 68–70° C.

v. (S)-5,6-dimethoxy-N-[(1-ethyl-2-pyrrolidinylmethyl)-3-propylsalicylamide] and isomer (S)-2,5-dimethoxy-N-[(1-ethyl-2-pyrrolidinylmethyl)-3-propylsalicylamide]: A solution of (iv) (10.0 g, 0.027 mmol) and HCl (0.027 mol in $Et_2O$) in 250 ml of $CH_2Cl_2$ was treated with $BBr_3$ (6.8 g, 0.027 mol) in 50 ml of $CH_2Cl_2$ at 10° C. The reaction mixture was stirred for 2 hours at 20° C. and quenched with 100 ml of 2M $NH_3$. Extraction with $CH_2Cl_2$, drying ($Na_2SO_4$), and evaporation of the solvent gave 9.2 g of (S)-5,6-dimethoxy-N-[(1-ethyl-2-pyrrolidinylmethyl)-3-propylsalicylamide] and isomer (S)-2,5-dimethoxy-N-[(1-ethyl-2-pyrrolidinylmethyl)-3-propylsalicylamide] in a ratio of 85:15. The residue was dissolved in 300 ml of $Et_2O$ and extracted with 50 ml of 1M NaOH twice, which removed the minor compound isomer (S)-2,5-dimethoxy-N-[(1-ethyl-2-pyrrolidinylmethyl)-3-propylsalicylamide from the ethereal layer. Drying and evaporation of the solvent gave 6.0 g (63%) of (S)-5,6-dimethoxy-N-[(1-ethyl-2-pyrrolidinylmethyl)-3-propylsalicylamide which was converted to 4.5 g (32%) of the L-tartarate: mp 84–85° C. (acetone/water 98:2); $^{13}C$ NMR (base, $CDCl_3$) δ 170.2, 154.9, 146.3, 143.6, 126.7, 119.9, 107.5.

The combined aqueous layer was washed with 50 ml of $Et_2O$ twice. The pH was adjusted to 8.5 and extraction with $Et_2O$ gave 1.3 g (14%) of pure isomer (S)-2,5-dimethoxy-N-[(1-ethyl-2-pyrrolidinylmethyl)-3-propylsalicylamide as an oil: $^{13}C$ NMR (base, $CDCl_3$) δ 170.1, 151.8, 149.9, 145.8, 123.9, 115.8, 107.9.

In above, β-asarone isolated from *Acorus calamus* plant is found to be a starting material for salicylamide based antipsychotic drug. The use of the oil for the synthesis of drug has been reported in the art. 4-allyl-1,2,6-trimethoxybenzene (elemicin) isolated from *Cymbopogon pendulus* plant, is used as a starting material for an antibacterial drug trimethoxyprim (Shahi, A. K; Sharma, S. N. and Tava, A., J. of Essential Oil Research 9(5):561–563 (1997)). However, for the first time a plant based toxic compound β-asarone is found to be a starting material for the synthesis of salicylamide based antipsychotic drug.

In the development of the invention, β-asarone was first isolated from *Acorus calamus* and then subjected to catalytic reduction. It was then realised that isolation of β-asarone from *Acorus calamus* was not necessary since it was observed that direct reduction of calamus oil could be performed with the dual benefit of not requiring isolation of β-asarone as well as resulting in the desired product 1-Propyl-2,4,5-trimethoxybenzene with a good yield. In addition, it was found that all three asarones give the same reduced product as the chemical structures of all three asarones (α, β and γ-asarone) found in calamus oil have the same molecular formula ($C_{12}H_{16}O_3$), the only difference being in the position of the double bond. The literature survey also supported the formation of same reduced dihydro products such as dihydrosafrole, dihydroeugenol, dihydroanethole and dihydrostilbene derivatives after reduction of corresponding either of the α,β and/or γ-isomers (Steffen, A., In: Perfume and Flavor Chemicals, Allured Publishing Corporations 362 South Schmate Road, Carol Stream, Ill., U.S.A. (1994) and Cushman, M.; Nagaranthnam, D., Gopal, D.; Hu-ming, H.; Lin, C. M.; and Hamel, E., J. Med. Chem. 35:2293–2306 (1992)).

It was observed during the course of development of the invention, that in fact, catalytic hydrogenation of whole calamus oil, which contains upto 90% of asarones including α, β and γ-asarone, gave a high yield of product 1-Propyl-2,4,5-trimethoxybenzene as all three asarones produce the same reduced dihydro product. Column purification of reduced calamus oil gave 1-Propyl-2,4,5-trimethoxybenzene with sweet and pleasant aroma. In addition, reduced calamus oil itself was found to possess a honey and rosy aroma, which is totally different from the distinctive smell of 1-Propyl-2,4,5-trimethoxybenzene. Therefore, both 1-Propyl-2,4,5-trimethoxybenzene or reduced calamus oil are capable of utilisation in flavour, perfumery and pharmaceutical industries.

There has been a lot of research on the effect of the substituents and functional groups which make a substance toxic or eliminate the toxicity. Any chemical substance that is electrophilic or metabolized to electrophilic species are often quite toxic, because electrophilic substances can react covalently with nucleophilic substituents of cellular macromolecules such as DNA, RNA, enzymes and proteins. These irreversible covalent interactions with important cellular macromolecules interfere with the macromolecule's function and can lead to a variety of toxic effects including cancer, hepatotoxicity, reproductive toxicity and developmental toxicity. It has been realised that the side chain of β-asarone contains carbon-carbon double bond, which can be metabolized to epoxide. The epoxide so formed is highly electrophilic and is capable of interacting with biological tissues, and could therefore, be the reason for the toxicity of β-asarone. In view of the above fact, it was possible to reduce the toxicity of β-asarone by hydrogenating the side olefinic bond into 1-propyl-2,4,5-trimethoxybenzene having a single bond as a side chain. The toxicity of the reduced calamus oil as well as of 1-Propyl-2,4,5-trimethoxy-benzene was tested. Toxicity test was performed on albino mice (body weight 25±2 g). 1-Propyl-2,4,5-trimethoxy-benzene was administered intraperitoneally (I.P.) and the animals were observed for 24 hr. Where the initial pilot dose was lethal, the sample was diluted. This was the acute toxicity test for maximum tolerance dose (MTD) as a single dose. It was noted that 1-Propyl-2,4,5-trimethoxybenzene was nearly five times (maximum tolerant doses, 0.56 ml/kg b.w.) less toxic than β-asarone (0.12 ml/kg b.w.) while whole reduced (hydrogenated) calamus oil (0.20 ml/kg b.w.) had half toxicity than the calamus oil (0.10 ml/kg b.w.). It must be noted that further reduction in toxicity is possible by further dilution as the odor intensity of 1-Propyl-2,4,5-trimethoxybenzene and reduced calamus oil is substantially stronger than both β-asarone and calamus oil.

The above process is also applicable for not only calamus oil but also to reduce the toxicity of several other plants that are rich in α, β and/or γ-asarone, such as *Heterotropa yakusimensis* for α-asarone (Saiki, Y.; Fukuyama, E. and Tsuneya, T., Yakugaku Zasshi 107(3), 219–226 (1987)) in 77%, *Asarum europaeum* for β-asarone (Rams, B., Herba Hungarica 22(1): 13–19 (1983)) in 70%, and *Crowea angustifolia* for γ-asarone (Garg, S. N., Agarwal, S. K. and Duhan, S. P. S., J. Essential Oil Research 5(2): 139–142 (1993) and Brophy J. J; Goldsack, R. J., Punruckvong, A.; Forster, P. I.; and Fookes, C. J. R., J. Essential Oil research 9(4):401–409 (1997)) in 68%, while obtaining a new kind of aroma.

The detailed toxicity test on animals, odour evaluation of product 1-Propyl-2,4,5-trimethoxybenzene and use of 1-Propyl-2,4,5-trimethoxybenzene as an intermediate for the synthesis of various other drugs are in progress which will further enhance the applications of the present invention as well as of *Acorus calamus* plant of tetraploid and hexaploid origin.

The following examples are given by way of illustration of the present invention and should not be construed to limit the scope of the present invention.

EXAMPLE 1

Plant Material and Chemicals: The plant material was collected in March–April 1999 from Palampur (H.P.) and was confirmed as 'Acorus calamus Linn' by comparison with the specimen (IHBT no. 1066) kept in the herbarium of our Institute. The hydrodistillation of rhizomes of *Acorus calamus* gave pungent smelling oil in 1.7% yield (w/w) with a presence of 81–85% β-asarone (by GC). α-asarone is procured from Sigma chemical s (U.S.A) and is used as an authentic sample.

Isolation of β-asarone from *Acorus calamus:* The pale yellow calamus oil (17.00 g) was chromatographed over silica gel using hexane as eluent to remove unwanted non-polar compounds. Subsequent elution with hexane-benzene mixture with increasing proportion of benzene gave a pure liquid 13.94 g in 82% yield (w/w) with $R_f$ 0.63 on silica gel TLC plate (hexane:benzene/toluene:ethylacetate:: 1:1:0.1) whose electrospray (ES)-mass spectrum gave a molecular ion at m/e 208 (M+, 100), 193 ($M^+$-Me, 46), 165 ($M^+$-$C_3H_7$, 24), suggesting that molecular formula $C_{12}H_{16}O_3$ in good agreement with the observation of 12 signals with peak at δ 125.5 (C-1'), 124.7 (C-2') and 14.5 (C-3') for side propenyl group and rest carbons at 151.4 (C-2), 148.5 (C-4), 142.3 (C-5), 118.0 (C-1), 114.1 (C-6), 97.6 (C-3) and 56.5, 56.2 & 55.9 (3-$OCH_3$) on the $^{13}$C NMR (CDCl$_3$, 75.4 MHz). The IR spectrum showed strong absorption at 1608 cm$^{-1}$, indicating the presence of an olefinic group and rest are at 2937, 2835, 1583, 1512, 1465, 1321, 1213, 1119, 1037, 965 and 859 cm$^{-1}$. The $^1$H NMR (CDCl$_3$, 300 MHz) signals showed a dd at δ 6.50 (1H, J=15.8 Hz and 1.5 Hz, H-1'), dq at 5.78 (1H, J=6.5 Hz and 15.8 Hz, H-2') and 1.85 (3H, dd, J=6.5 Hz and 1.5 Hz, H-3') due to proton of propenyl side chain and rest protons at 6.84 (1H, s, H-6), 6.53 (IR, s, H-3), and 3.88, 3.83 and 3.79 (s, 3H, each, 3-$OCH_3$). UV λmax MeOH nm (log ε): 269 (2.36), 301 (4.01). On the basis of above spectral data and comparing with reported literature (Gonzalez, M. C., Sentandrew, M. A.; Rao, K. S., Zafra, M. C. and Cortes, D., Phytochemistry 43:1361–1364 (1996)), the liquid was identified as β-asarone in 94% purity (by GC) (FIG. 2)

Synthesis of 1-Propyl-2,4,5-trimethoxybenzene from β-asarone: The β-asarone (6.00 g, 0.029 mol) in 160 ml of ethanol is stirred with 10% palladium on activated charcoal (0.80 g) and ammonium formate (17.00 g, 0.27 mol) at room temperature under nitrogen atmosphere till the disappearance of starting material. The catalyst was removed by filtration and the solvent was evaporated under reduced pressure. The residue was partitioned between ethyl acetate and water and the ethyl acetate layer washed with water, dried (Na$_2$SO$_4$) and filtered. Evaporation of filtrate left a liquid, which was chromatography, on silica gel using hexane-benzene mixture with increasing proportion of benzene as the eluent. The eluate was evaporated to give 5.87 g (97%) of a clear sweet and pleasant liquid with $R_f$ 0.69 (hexane:benzene/toluene:ethylacetate:: 1:1:0.1) which solidified below 0° C. The $^1$H NMR (DMSO-d6) of liquid showed an expected shift of proton of propyl side chain which appeared at δ d 2.5 (2H, t, C-1'), 1.6 (2H, m, C-2') and 0.9 (3H, t, C-3') and rest protons at 6.72 (1H, s, H-6), 6.62 (1H, s, H-3) and 3.76 to 3.68 (9H, s, 3-$OCH_3$). The mass spectrum of liquid showed a molecular ion at m/e 210 ($M^+$, 39), 181 ($M^+$-$C_2H_5$, 100), 167 ($M^+$-$C_3H_7$, 5), 151 ($M^+$-$OCH_3$+CO, 29), 136 ($M^+$-$C_3H_7$+$OCH_3$, 10) which IR spectrum showed strong absorption at 2958, 2870, 1512, 1464, 1398, 1205, 1124, 1040, 978 and 843 cm$^{-1}$ with disappearance of olefinic absorption (1608 cm$^{-1}$). $^{13}$C NMR (CDCl$_3$) of liquid also showed expected shift of propyl side signals of C-1', C-2' and C-3' which appeared at δ 31.6 (C-1'), 23.3 (C-2') and 13.79 (C-3') and rest at δ 151.4 (C-2), 147.4 (C-4), 142.7 (C-5), 122.7 (C-1), 114.3 (C-6), 98.0 (C-3) and 56.5, 56.2 & 56.0 (3-$OCH_3$). UV λmax MeOH nm (log ε): 288 (4.28). A shift by 13 nm in UV-vis spectra of product was observed from 301 nm to 288 nm (as conjugation of double bond of starting material asarone was reduced to single bond) with complete disappearance of peak 269 nm (FIG. 1). On the basis of 1H NMR (FIG. 4), $^{13}$C NMR (FIG. 5) and Mass (FIG. 6) spectral data, the above liquid was identified as 1-Propyl-2,4,5-trimethoxybenzene in 99% purity (by GC) (FIG. 3).

Synthesis of 1-Propyl-2,4,5-trimethoxybenzene from crude oil of *Acorus calamus:*

In this method 42.00 g of crude calamus oil in 300 ml methanol was hydrogenated with 10% Pd/C (4.80 g) at 10–40 psi at room temperature till the disappearance of starting material. The catalyst was filtered and the solvent was removed under reduced pressure, which afforded 39.9 g (95 w/v) of reduced oil. Column purification of reduced oil on silica gel column using above eluent system (hexane-benzene mixture) gave a liquid 35.76 g in 85% yield (w/w). The 1H NMR (CDCl$_3$) of liquid appeared at δ d 2.4 (2H, t, C-1'), 1.6 (2H, m, C-2'), 0.9 (3H, t, C-3'), 6.81 (1H, s, H-6), 6.32 (1H, s, H-3) and 3.84 to 3.78 (9H, s, 3-$OCH_3$). The GC, Mass spectra and UV-vis spectra of liquid confirmed the formation of 1-Propyl-2,4,5-trimethoxybenzene of formula I.

The main advantages of the present invention are
1. A simple and economical process to convert an internationally banned toxic compound β-asarone or calamus oil into useful and less toxic products.
2. Introduction of a new kind of sweet, fruity, rosy and spicy aroma molecule better than the original pungent smell of calamus oil for application in flavour, perfumery and pharmaceutical industries.
3. Discovery of a product 1-Propyl-2,4,5-trimethoxybenzene as an inexpensive and simple starting material for salicylamide based antipsychotic drug.
4. The present chemical process can increase the price of calamus oil as demand of new products go up as presently, calamus oil of tetraploid or hexaploid varieties distributed extensively in Asian origin) has very low price in comparison to the oil of diploid and triploid (distributed in American or European origin) varieties.
5. A process of converting asarones rich plants such as *Asarum europaeum, Crowea angustifolia* and *Heterotropa yakusimensis* into useful and non-toxic products.
6. A simple process by which a toxic compound β-asarone present upto 70 to 90% in tetraploid or hexaploid varieties (distributed extensively in Asian countries) of *Acorus calamus* is converted into useful product 1-Propyl-2,4,5-trimethoxybenzene.
7. A simple process for isolation of β-asarone in high purity from *Acorus calamus* oil by column chromatography affording above 90% purity, more than the purity (70%) claimed by Aldrich and Fluka catalog chemicals.
8. A simple process for the preparation of 1-Propyl-2,4,5-trimethoxybenzene by catalytic reduction of above isolated β-asarone.
9. An inexpensive process for the preparation of 1-Propyl-2,4,5-trimethoxybenzene by direct reduction of calamus oil in which percentage of asarones (including α, β and γ-asarone) go up to 90 percentage in tetraploid or hexaploid varieties of *Acorus calamus* oil.
10. Scope for commercialisation of a product 1-Propyl-2,4,5-trimethoxybenzene and reduced calamus oil in flavour, perfumery and pharmaceutical industries since both products have a new kind of sweet, fruity, spicy and honey and rosy aroma respectively.
11. A process for minimizing the toxicity of an internationally banned calamus oil of tetraploid or hexaploid varieties for re-utilisation as toxicity of the reduced calamus oil and 1-Propyl-2,4,5-trimethoxybenzene is found to be two to five times less than calamus oil and β-asarone respectively.
12. A single step process to obtain two fold benefits by reduction in toxicity and improvement in aroma better than the original pungent aroma of calamus oil.
13. 1-Propyl-2,4,5-trimethoxybenzene is an inexpensive, high yielding and simple starting material for important 3-propyl-5,6-dimethoxysalicylamide based antipsychotic drug. The reported prior art synthesis of salicylamide derivative requires several steps in which intermediate 1-Propyl-2,4,5-trimethoxybenzene itself is synthesised in two steps by using Friedel-Craft acylation of an expensive material 1,2,4-trimethoxybenzene with propylchloride followed by reduction. Provide above simple process of reduction to convert other asarone rich plants such as *Asarium europaeum, Crowea angustifolia* and *Heterotropa yakusimensis* into useful products such as 1-Propyl-2,4,5-trimethoxybenzene.

We claim:
1. A composition having the aroma of honey and roses selected from the group consisting of mouthwash, toothpaste, antiseptic or toiletry soap, shaving cream and tobacco products, said composition containing an amount of hydrogenated or reduced calamus oil sufficient to import thereto a pleasantly sweet honey and rose aroma, said hydrogenated or reduced calamus oil having reduced toxicity as compared to unhydrogenated or unreduced calamus oil.

* * * * *